United States Patent [19]

Bortinger

[11] Patent Number: 5,446,000
[45] Date of Patent: Aug. 29, 1995

[54] TREATMENT FOR VIRGIN PHOSPHOROUS/VANADIUM OXIDATION CATALYSTS

[75] Inventor: Arie Bortinger, Ridgewood, N.J.

[73] Assignee: Scientific Design Company, Inc., Little Ferry, N.J.

[21] Appl. No.: 209,407

[22] Filed: Mar. 14, 1994

Related U.S. Application Data

[63] Continuation of Ser. No. 24,320, Mar. 1, 1993, Pat. No. 5,348,927.

[51] Int. Cl.⁶ ............................................. B01J 20/34
[52] U.S. Cl. ........................................ 502/38; 502/51; 502/52; 502/55; 502/515; 423/488
[58] Field of Search ................... 502/341, 38, 55, 515; 423/488

[56] References Cited

U.S. PATENT DOCUMENTS

| | | | |
|---|---|---|---|
| 3,926,852 | 12/1975 | Cahen et al. | 502/209 |
| 4,510,259 | 4/1985 | Udovich et al. | 502/210 |
| 5,348,927 | 9/1994 | Bortinger | 502/51 |

*Primary Examiner*—Anthony McFarlane
*Attorney, Agent, or Firm*—Kenneth H. Johnson

[57] ABSTRACT

A method of removing chloride from phosphorus/vanadium/oxygen mixed oxide oxidation catalysts comprising treating a chloride containing catalyst comprising phosphorus, vanadium and oxygen with a stream of gas comprising oxygen, steam and an inert gas at flow rate and temperature and for a period of time to substantially reduce the amount of chloride in the catalyst.

11 Claims, 1 Drawing Sheet

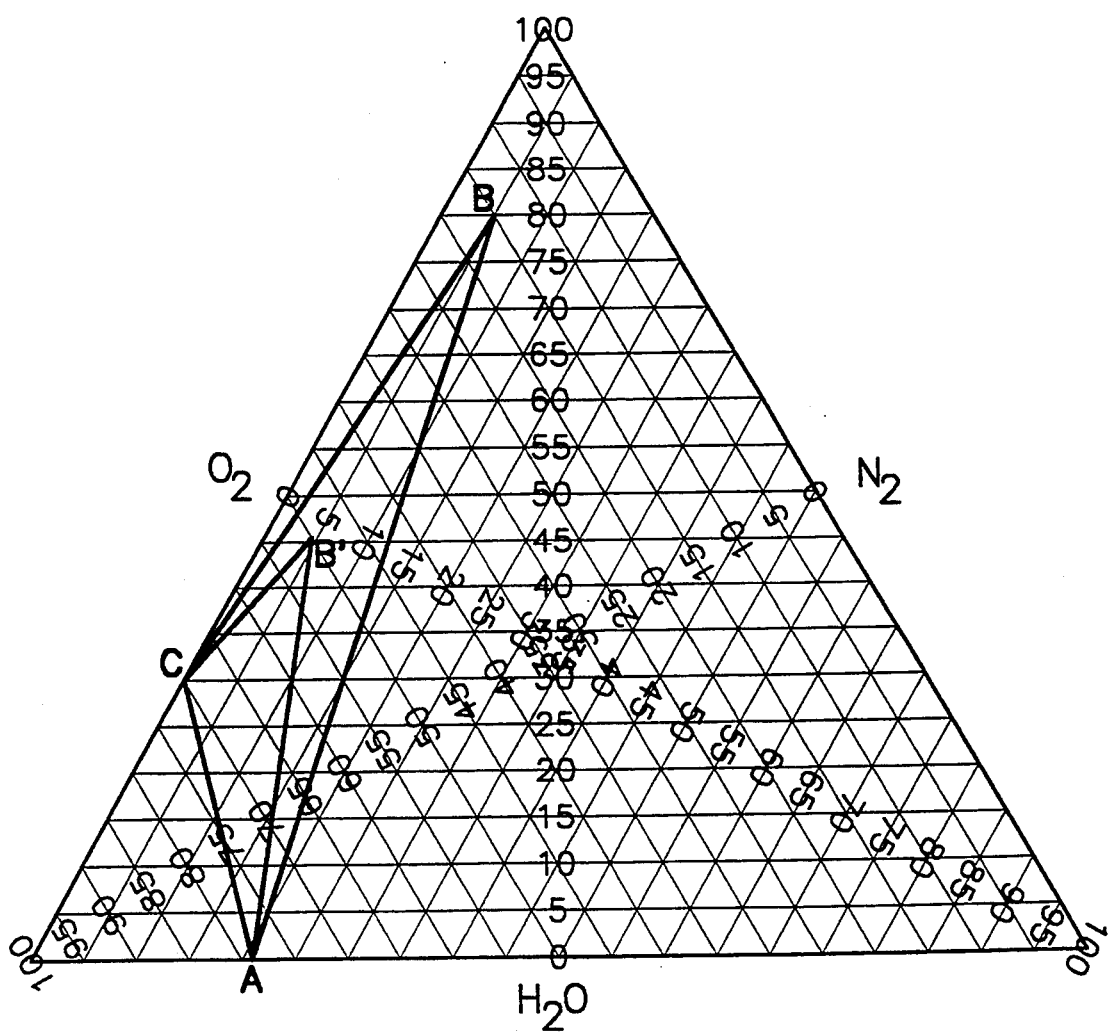

TREATMENT FOR VIRGIN PHOSPHOROUS/VANADIUM OXIDATION CATALYSTS

This is a continuation of application Ser. No. 08/024,320, filed Mar. 1, 1993 now U.S. Pat. No. 5,348,927.

BACKGROUND OF THE INVENTION

The present invention relates to a treatment for virgin PVO catalyst used in the partial oxidation of hydrocarbons to prepare dicarboxylic acids and anhydrides. The present invention is directed to PVO catalyst prepared by procedures that employ an HCl reduction step to produce the reduced vanadium. Most particularly, the invention relates to a process for reducing the chloride content in the PVO catalyst.

Basically, all of the methods used to prepare oxidation catalysts seek to obtain vanadium in a valence state of less than +5. One method of achieving this is to begin with vanadium in less than the +5 valence state. Another method and that used most widely in the art is to start with vanadium in the +5 state and reduce the valency to less than +5. This invention relates to the latter method. Several variations on this method have been used to obtain these catalyst. In one method $V_2O_5$ is reduced in a solution with HCl to obtain vanadyl chloride. A typical catalyst preparation may involve dissolving the vanadium, phosphorus, and other components in a common solvent. The reduced vanadium with a valence of less than 5 is obtained by initially using a vanadium compound with a valence of plus 5 such as $V_2O_5$ and thereafter reducing to the lower valence with,, for example, hydrochloric acid during the catalyst preparation to form the vanadium oxysalt, vanadyl chloride, in situ. The vanadium compound is dissolved in a reducing solvent, such as hydrochloric acid. The solvent functions not only to form a solvent for the reaction, but also to reduce the valence of the vanadium compound to a valence of less than 5. Preferably, the vanadium compound is first dissolved in the solvent and thereafter the phosphorus and other components, if any, are added. The reaction to form the complex may be accelerated by the application of heat. The complex formed is then, without a precipitation step, deposited as a solution onto a carrier and dried. Generally, the average valence of the vanadium will be between about plus 2.5 and 4.6 at the time of deposition onto the carrier.

In another method the catalyst is prepared by precipitating the metal compounds, either with or without a carrier, from a colloidal dispersion of the ingredients in an inert liquid. In some instances the catalyst may be deposited as molten metal compounds onto a carrier. The catalysts have also been prepared by heating and mixing anhydrous forms of phosphorus acids with vanadium compounds and other components. In any of the methods of preparation, heat may be applied to accelerate the formation of the complex.

A method of obtaining vanadyl chloride was disclosed by Koppel et al, Zeit. anorg. Chem, 45, p. 346-351, 1905 by the reduction of $V_2O_5$ in alcoholic HCl solution. This method has been recommended for the preparation of the phosphorus-vanadium oxidation catalyst for example, by Kerr in U.S. Pat. No. 3,255,211 where the solvent also serves as the reducing agent. Subsequently, U.S. Pat. Nos. 4,017,521; 4,043,943; 4,251,390; 4,283,307 and 4,418,003 for example, employed this method generally referred to as the "anhydrous process" of reducing vanadium to prepare the basic phosphorus-vanadium catalyst. The catalysts produced by this latter method have been found to be generally superior to similar catalyst by the other methods. Specifically what had occurred to this class of oxidation catalysts prior to the return to the anhydrous process had been the addition of a veritable cornucopia of elements to the base vanadium-phosphorus composition, see for example U.S. Pat. No. 4,105,586 where in addition to V, P and O the catalyst must contain nine other elements. The catalyst were satisfactory, but manufacturing was difficult because of the number of components and their varying effects on the catalyst performance.

Many references disclose oxidation catalysts which are suitable for producing maleic anhydride by the partial oxidation of n-butane, which catalysts contain molybdenum as one component of a phosphorus, vanadium mixed oxide catalyst. For example U.S. Pat. No. 3,980,585 discloses a catalyst containing P, V Cu and one of Te, Zr, Ni, Ce, W, Pd, Ag, Mn, Cr, Zn, Mo, Re, Sn, La, Hf Ta, Th, Ca, U or Sn; and U.S. Pat. No. 4,056,487 discloses a PVO catalyst containing Nb, Cu, Mo, Ni, Co and plus one or more of Ce, Nd, Ba, Hf, U, Ru, Re, Li or Mg. U.S. Pat. No. 4,515,904 discloses a procedure for preparing PVO catalysts which may include one metal of Mo, Zn, W, U, Sn, Bi, Ti, Zr, Ni, Cr or Co in atomic ratios of metal: V of 0.001 to 0.2:1.

U.S. Pat. No. 4,147,661 discloses high surface area PVO mixed oxide catalyst additionally containing W, Sb, Ni and/or Mo at atomic ratios of 0.0025 to 1:1 to vanadium.

U.S. Pat. No. 4,418,003 discloses PVO catalysts containing either Zn or Mo which is deactivated by Na or Li and which may also contain Zr, Ni, Ce, Cr, Mn, Ni and Al.

Commonly assigned U.S. Pat. No. 5,070,060 discloses an oxidation catalyst which contains molybdenum which produces a more stable catalyst.

The use of an HCl reduction step to produce the reduced vanadium from +5 vanadium is the most widely used commercial procedure for preparing the PVO catalysts. Even after calcination to prepare the catalyst, residual chloride ions remain in the virgin catalyst. As the term is used here "virgin" or "fresh" PVO catalyst refers to a catalyst that has not been activated for use or used in a partial oxidation process.

The chloride previously were removed during the catalyst activation period in the reactor, but their release from the solid catalyst in to the reactor and the downstream equipment in the process can cause sever problems. The main problems are: equipment corrosion and colored products, which in turn results in poor product quality and/or product loss and eventually producing an increased waste disposal. Thus, the problem is to remove the chloride at the point of catalyst manufacture or at least before it is exposed to hydrocarbon feed in the reactor. However, any procedure that is employed to remove the chloride prior to activation must not result in a detrimental change in the catalyst per se and in particular not oxidize or reduce the vanadium component of the virgin catalyst, which preferably has a valence of around 4+ in virgin catalyst.

It is an advantage of the present invention that the chloride can be removed from the virgin PVO catalyst without detriment to the catalyst. It is a further advantage that the valence of the vanadium remains in the preferred range. These and other advantages and features will become apparent from this disclosure. It is a particular advantage that the present method is especially suitable for removal of high percentages of low concentrations of chloride.

SUMMARY OF THE INVENTION

The present invention is a method of removing chloride from phosphorus/vanadium/oxygen mixed oxide oxidation catalysts comprising treating a chloride containing catalyst comprising phosphorus, vanadium, other promoters and oxygen with stream of gas comprising from greater than 0 to less than 100% oxygen, from greater than 0 to less than 100% steam and from greater than 0 to less than 100% of an inert gas at a temperature and for a period of time to substantially reduce the amount of chloride in the catalyst. Preferably the oxygen comprises 0.1 to 15.0 vol. % of the gas stream; the steam comprise 0.5 to 90.0 vol. % of the gas stream; and the inert gas comprises 0.1 to less than 100.0 vol. % of the gas stream. Preferably the temperature of the treatment is from 250° to 420° C. for 0.5 to 24 hours.

The term "inert gas" as used herein means nitrogen, helium, argon or mixtures thereof. The preferred valence of the vanadium in the treated catalyst is in the range of 3.5 to 4.5 and more preferably 3.7 to 4.2. The present process is useful for removing not only large percentages of chloride, e.g. in excess of 50%, usually 70 to over 90%, but in removing substantially all of the chloride even when only small quantities are initially present.

BRIEF DESCRIPTION OF THE DRAWING

The FIGURE is a triangular graphical representation showing a preferred ranges of steam, oxygen and inert content of the gas used in the present invention.

DETAILED DESCRIPTION AND PREFERRED EMBODIMENTS

The present invention comprises a method of removing chloride from a phosphorous/vanadium/oxygen catalyst by treating the catalyst with a stream of gas comprising oxygen, steam and an inert gas at a flow rate and temperature and for a period of time to substantially reduce the amount of chloride in the catalyst. The present process is particularly suitable for removing low concentrations of chloride from the catalysts, i.e., initial concentrations of chloride below 2 weight percent, preferably less than 1 weight percent with the residual chloride content being less than 500 ppm, preferably less than 350 ppm.

Preferred catalysts are produced by the process comprising reducing vanadium in the +5 valence state in a substantially anhydrous organic medium to a valence of less than +5 and digesting said reduced vanadium in concentrated phosphoric acid. The resultant catalyst complex is characterized as a mixed oxide, however, the structure of the complex has not been determined but may be conveniently represented by a formula such as:

a is 0.90 to 1.3. Me is a metal, alkali metal or alkaline earth metal as known in the art as modifiers for catalysts of this type. This representation is not an empirical formula and has no significance other than representing the atom ratio of the components of the catalyst. The x and y in fact, have no determinate value and can vary widely depending on the combinations within the complex. That there is oxygen present is known, and the $O_x$ is representative of this. Suitable dried catalysts have a crystallinity of 30 to 90%, preferably at least 40%.

In a preferred embodiment the improved catalyst comprise in addition to P, V and O, Zn, Li, and Mo is that produced from an alcoholic solution reduction of vanadium pentoxide wherein the organic solvent is an alcohol and the reduction of the vanadium is obtained by contacting it with HCl. This is conveniently carried out by passing gaseous HCl through the alcohol having the vanadium pentoxide suspended therein. The vanadium pentoxide is reduced by the HCl and brought into solution as the vanadyl chloride. The completion of the reduction is the appearance of a dark reddish brown solution. Hydrogen bromide would be about the same as a reducing agent in this system. It is preferred that the reduction temperature should be maintained at no greater than 60° C. and preferably less than 55° C. Optimally active catalyst are the result when the reduction is carried out temperatures in the range of about 35° C. to 55° C., preferably 37° C. to 50° C.

Generally in the catalyst preparation from 2500 to 4400 ml of alcohol, preferably 2700 to 4200 ml per pound of $V_2O_5$ and from 1.5 to 3.0 pounds of HCl per pound of $V_2O_5$ are employed.

To obtain the mixed oxides of vanadium and phosphorus, phosphoric acid of approximately 99% $H_3PO_4$ (98 to 101%) is added, for example, prepared from 85% $H_3PO_4$ and $P_2O_5$ or commercial grades of 105 and 115% phosphoric acid diluted with 85% $H_3PO_4$ or water to the final required concentration of $H_3PO_4$ and the vanadium compound digested which is discerned by a change in the color of the solution to a dark blue green. The alcohol is then stripped off to obtain the dried catalyst.

The digestion of the vanadium compound in the phosphoric acid is normally conducted at reflux until the color change indicated the completed digestion.

The final removal of alcohol is usually carried out in an oven at a temperature in the range of 110° to 170° C. Reduced pressure can also be applied to lower oven temperatures. Generally calcination or roasting of the dried catalyst will be at a temperature in the range of 200° to 400° C. for a sufficient period to improve the catalytic properties of the composition.

The temperatures employed are relatively low hence the term calcination may not be appropriate. In any event, heating the composition under these temperature conditions has been found beneficial. The calcination is preferably carried out to produce materials having a characteristic powder x-ray diffraction ratio.

The resultant preferred catalyst complex is characterized as a mixed oxide, however, the structure of the complex has not been determined but may be conveniently represented by a formula such as:

a is 0.90 to 1.3, b is 0.001 to 0.15, c is 0.005 to 0.10 and d is 0.001 to 0.15.

The organic solvent is preferably a primary or secondary alcohol such as methanol, ethanol, 1-propanol, 2-propanol, butanol, 2-butanol, 2,methyl-1-propanol, 3-methyl-2-butanol, 2,2-dimethyl-1-propanol, 1-hexanol, 4-methyl-1-pentanol, 1-heptanol, 4-methyl-1-hexanol, 4-methyl-1-heptanol, 1,2-ethanediol, glycerol, trimethylopropane, 4-methyl 2-pentanone, diethylene glycol and triethylene glycol or mixtures thereof. The alcohol is also a mild reducing agent for the vanadium +5 compound. A preferred cosolvent system comprises 2-butanol and from 5-50 vol % of the cosolvent.

Generally the atomic ratio of Zn to vanadium is in the range of 0.001 to 0.15:1, however it has been found that lower ratios of zinc/vanadium produce the most active catalyst and compositions containing Zn/V mole ratio in the range of 0.01 to 0.07 are preferred.

The phosphorus is generally present in these catalyst as well as those of the prior art in the mole ration of P/V 0.09-1.3/1. Optimum ratios P/V are found to be below 1.22/1 and above 1.0/1. The stabilizing effect of Mo allows the use of less phosphorus than otherwise comparable prior art catalyst and the concomitant benefit that phosphorus loss and the resulting deactivation of the catalyst in reactor operation is reduced, i.e., longer time trend (reactivity vs hours on stream).

The lithium component is present at an atomic ratio of 0.001 to 0.15:1, Li:V.

The lithium and zinc modifier components are added as the compounds thereof such as acetates, carbonates, chlorides, bromides, oxides, hydroxides, phosphates and the like e.g., zinc chloride, zinc oxide, zinc oxalate, lithium acetate, lithium chloride, lithium bromide, lithium carbonate, lithium oxide, or lithium orthophosphate and the like.

The molybdenum compound may dissolved in an organic solvent, as described above or water and added to the reaction mixture. The solvent containing the molybdenum compound may be added either with the other modifiers or at different time. If water is used the solvent containing the molybdenum compound is preferably added after the first digestion and prior to the second digestion. The use of a soluble molybdenum compound dissolved in a solvent according to the present invention for addition to the reaction mixture has been found to be particularly effective in dispersing the molybdenum throughout the mixture and the final dried catalyst. Some examples of suitable soluble molybdenum catalyst include phosphomolybdic acid, ammonium molybdate (VI) tetrahydrate, lithium molybdate, molybdenum tetrabromide, molybdenum trioxyhexachloride and the like.

The catalyst may be employed as pellets, disc, flakes, wafers, or any other convenient shape which will facilitate its use in the tubular reactors employed for this type of vapor phase reaction. For example the catalyst may be prepared as tablets having a hole or bore therethrough as disclosed in U.S. Pat. No. 4,283,307 which is incorporated herein. The material can be deposited on a carrier. Although fixed bed tubular reactors are standard for this type of reaction, fluidized beds are frequently used for oxidation reactions, in which case the catalyst particle size would be on the order of about 10 to 150 microns.

The use of this class of catalyst for the partial oxidation of $C_4$-$C_{10}$ hydrocarbons to the corresponding anhydrides is generally recognized. They have been widely considered for the conversion of normal $C_4$ hydrocarbons, both the alkane, n-butane, and alkene, n-butene, for the production of maleic anhydride, which has a wide commercial usage.

The oxidation of the n-$C_4$ hydrocarbon to maleic anhydride may be accomplished by contacting, e.g., n-butane in low concentrations in oxygen with the described catalyst. Air is entirely satisfactory as a source of oxygen, but synthetic mixtures of oxygen and diluent gases, such as nitrogen, also may be employed. Air enriched with oxygen may be employed.

The gaseous feed stream to the standard tubular oxidation reactors normally will contain air and about 0.5 to about 2.5 mole percent hydrocarbons such as n-butane. About 1.0 to about 2.0 mole percent of the n-$C_4$ hydrocarbon are satisfactory for optimum yield of product for the process of this invention. Although higher concentrations may be employed, explosive hazards may be encountered except in fluidized bed reactors where concentrations of up to about 4 or 5 mole % can be used without explosive hazard. Lower concentrations of $C_4$, less than about one percent, of course, will reduce the total productivity obtained at equivalent flow rates and thus are not normally economically employed.

The flow rate of the gaseous stream through the reactor may be varied within rather wide limits but a preferred range of operations is at the rate of about 50 to 300 grams of $C_4$ per liter of catalyst per hour and more preferably about 100 to about 250 grams of $C_4$ per liter of catalyst per hour. Residence times of the gas stream will normally be less than about 4 seconds, more preferably less than about one second, and down to a rate where less efficient operations are obtained. The flow rates and residence times are calculated at standard conditions of 760 mm. of mercury and at 25° C. A preferred feed for the catalyst of the present invention for conversion to maleic anhydride is a n-$C_4$ hydrocarbon comprising a predominant amount of n-butane and more preferably at least 90 mole percent n-butane.

A variety of reactors will be found to be useful and multiple tube heat exchanger type reactors are quite satisfactory. The tubes of such reactors may vary in diameter from about ¼ inch to about 3 inches, and the length may be varied from about 3 to about 10 or more feet. The oxidation reaction is an exothermic reaction and, therefore, relatively close control of the reaction temperature should be maintained. It is desirable to have the surface of the reactors at a relatively constant temperature and some medium to conduct heat from the reactors is necessary to aid temperature control. Such media may be Woods metal, molten sulfur, mercury, molten lead, and the like, but it has been found that eutectic salt baths are completely satisfactory. One such salt bath is a sodium nitrate-sodium nitrite-potassium nitrite eutectic constant temperature mixture. An additional method of temperature control is to use a metal block reactor whereby the metal surrounding the tube acts as a temperature regulating body. As will be recognized by one skilled in the art, the heat exchange medium may be kept at the proper temperature by heat exchangers and the like. The reactor or reaction tubes may be iron, stainless steel, carbon-steel, nickel, glass tubes such as Vycor and the like. Both carbon steel and nickel tubes have excellent long life under the conditions for the reactions described herein. Normally, the reactors contain a preheat zone of an inert material such as ¼ inch Alundum pellets, inert ceramic balls, nickel balls or chips and the like, present at about one-half to one-tenth the volume of the active catalyst present.

The temperature of reaction may be varied within some limits, but normally the reaction should be conducted at temperatures within a rather critical range. The oxidation reaction is exothermic and once reaction is underway, the main purpose of the salt bath or other media is to conduct heat away from the walls of the reactor and control the reaction. Better operations are normally obtained when the reaction temperature employed is no greater than about 100° C. above the salt bath temperature. The temperature in the reactor, of course, will also depend to some extent upon the size of the reactor and the C4 concentration. Under usual operating conditions, in a preferred procedure, the temperature in the center of the reactor, measured by thermocouple, is about 365° C. to about 550° C. The range of temperature preferably employed in the reactor, measured as above, should be from about 380° C. to about 515° C. and the best results are ordinarily obtained at temperatures from about 380° C. to about 430° C. Described another way, in terms of salt bath reactors with carbon steel reactor tubes about 1.0 inch in diameter, the salt bath temperature will usually be controlled between about 350° C. to about 550° C. Under normal conditions, the temperature in the reactor ordinarily should not be allowed to go above about 470° C. for extended lengths of time because of decreased yields and possible deactivation of the catalyst.

The reaction may be conducted at atmospheric, super-atmospheric or below atmospheric pressure. The exit pressure will be at least slightly higher than the ambient pressure to insure a positive flow from the reaction. The pressure of the inert gases must be sufficiently high to overcome the pressure drop through the reactor.

The maleic anhydride may be recovered in a number of ways well known to those skilled in the art. For example, the recovery may be by direct condensation or by adsorption in suitable media, with subsequent separation and purification of the maleic anhydride.

Examples 1-7

EXAMPLE 1

The following typical catalysts preparative procedure illustrate typical catalyst work up using the information discussed above. The tablets were made as follows:

3600 ml anhydrous isobutanol and 636 grams $V_2O_5$ were charged into a 2 gallon Pfaudler reactor equipped with a mechanical stirrer, a gas inlet tube, thermowell, Dean stark trap with a condenser, and a heating jacket. About 3.5 lb hydrogen chloride gas were bubbled into the stirred suspension. The reaction temperature was maintained at 40±3° C. To the resulting red-brown solution was added 9.5 grams anhydrous zinc chloride, 2.96 grams lithium chloride, 13.10 grams molybdenum trioxide and a solution of 794.8 grams of 99.3% phosphoric acid. An additional 1223 ml of anhydrous isobutanol were added to the reaction mixture, the ratio of gal isobutanol/lb $V_2O_5$ being about 0.91. The resulting solution was refluxed for 1 hour. At the end of this digestion period the alcohol was stripped until about 3600 ml distillate were removed resulting in a thick slurry. The thick slurry was then dried in an oven for 16 hours at 150° C. The dry cake was then crushed and calcined at 260° C. About 4% graphite was added and the graphite containing powder was used to fabricate 3/16"×3/16" tablets with a 1/16" hole struck therethrough. These tablets were used as the virgin V/P/O promoted catalysts in Examples 8 and 9.

EXAMPLE 2

The following method was used to synthesize the powdered catalysts which were treated for chloride removal in Examples 3-7.

The catalyst was prepared as in Example 1 except that the ratio of gal isobutanol/lb $V_2O_5$ was about 0.829. The thick slurry obtained after distilling off the isobutanol was dried and calcined as in Example 1. The calcined powder containing about 4% graphite was used in Examples 3-7.

EXAMPLES 3-7

These examples illustrate the removal of chloride from catalyst in a powder form prepared in Example 2.

About each 15 g of powder catalyst prepared in Example 2 were placed in a 22 mm ID quartz tube reactor which was heated by a Lindberg furnace. A flow of gas containing the desired components was heated and passed through the reactor. The original level of chloride in the sample was 0.7 wt %. The conditions and the amount of chloride removal are reported in TABLE I.

TABLE I

| EXAM. | 3 | 4 | 5 | 6 | 7 |
|---|---|---|---|---|---|
| TEMP. °C. | 375 | 375 | 375 | 375 | 375 |
| TIME, HRS. | 3 | 3 | 3 | 3 | 3 |
| % $O_2^1$ | 8 | 4 | 1.9 | 0 | 21 |
| % STEAM$^2$ | 46 | 43 | 33 | 30 | 0 |
| $V^{ox}$ | 4.2 | 4.0 | 4.0 | 3.5 | 4.5 |
| % Cl REMOVED | 97.9 | 91.1 | 75.4 | 50.6 | 70.0 |

$^1$% OXYGEN IN THE GAS STREAM BEFORE STEAM WAS INTRODUCED, THE BALANCE IS NITROGEN.
$^2$% STEAM OF THE TOTAL GAS FLOW THROUGH THE CATALYST BED.

EXAMPLES 8 AND 9

These examples illustrate the removal of chloride from a catalyst in a tablet form as prepared in Example 1.

The procedures of Example 3-7 were followed except that instead of the powders, the treatments were made on full tablets prepared in Example 1. The original level of chloride in the sample was 0.7 wt %. The conditions and the amount chloride removed and other results are reported in TABLE II.

TABLE II

| EXAM. | 8 | 9 |
|---|---|---|
| TEMP. °C. | 375 | 375 |
| TIME, HRS. | 3 | 3 |
| % $O_2^1$ | 3.5 | 3.5 |
| % STEAM$^2$ | 32 | 40 |
| $V^{ox}$ | 4.0 | 4.1 |
| % Cl REMOVED | 90.3 | 95.4 |

$^1$% OXYGEN IN THE GAS STREAM BEFORE STEAM WAS INTRODUCED, THE BALANCE IS NITROGEN.
$^2$% STEAM OF THE TOTAL GAS FLOW THROUGH THE CATALYST BED.

The FIGURE is a graphic representation of the most preferable ranges for steam, oxygen and nitrogen (inert). A suitable range according to present invention for combinations of steam, oxygen and inert fall within the area A-B-C on the triangular graph. The valence of the vanadium can range from 3.5 to 4.5, preferably 3.7 to 4.2. A preferred range falls within the area A-B'-C in FIG.1. The points A, B' and C all represent combinations of steam, oxygen and inert content that resulted in excellent chlorine removal (at least 75%) and yet left the vanadium in an oxidation state of from 3.9 to 4.2.

The virgin catalyst may be calcined as a powder, for example in an oven or in a fluidized bed; as a shaped article, for example as extrudates or pills; in a reactor or ex situ, prior to contact with hydrocarbon feed.

The reduced chloride content of the catalyst made according to the present invention is a significant improvement since chlorine in the catalyst tends to deteriorate reaction vessels and downstream equipment.

The invention claimed is:

1. A method of removing chloride from phosphorus/vanadium/oxygen mixed oxide oxidation catalysts comprising treating a chloride containing virgin catalyst wherein said chloride is introduced into said catalyst by using HCl as a reducing agent during the preparation of said catalyst and comprising phosphorus, vanadium, oxygen and up to 2.0 wt % chloride with a stream of gas comprising 0.1 to 15 vol % oxygen, 0.5 to 80 vol % steam and 0.1 to 80 vol % of an inert gas selected from the group consisting of nitrogen, helium, argon and mixtures thereof at flow rate and temperature and for a period of time to remove over 50% of chloride in the catalyst.

2. The method according to claim 1 wherein the temperature of the treatment is in the range of from 250° to 420° C.

3. The method according to claim 1 wherein the treatment is in the range of 0.5 to 24 hours.

4. The method according to claim 1 wherein the valence of the vanadium is between +3.5 and +4.5.

5. The method according to claim 1 wherein the valence of the vanadium is between +3.7 and +4.2.

6. The method according to claim i wherein said inert gas comprises nitrogen.

7. The method according to claim 1 wherein the phosphorus/vanadium/oxygen mixed oxide oxidation catalysts comprise a composition of the formula:

$$VP_aZn_bMo_cLi_dO_x$$

wherein a is 0.90 to 1.3, b is 0.001 to 0.15, c is 0.005 to 0.10 and d is 0.001 to 0.15 and x is an determinate number.

8. The method according to claim 1 wherein the catalyst is treated in the form of a powder before being fabricated into final tableted form.

9. The method according to claim 1 wherein the catalyst is treated in the form of tablets or other shapes.

10. A method of removing chloride from phosphorus/vanadium/oxygen mixed oxide oxidation catalysts comprising treating a chloride containing virgin catalyst prepared using HCl as the reducing agent for the vanadium and comprising phosphorus, vanadium, oxygen and up to 1.0 wt % chloride with a stream of gas comprising 0.1 to 15 vol. % oxygen, 0.5 to 90 vol. % steam and 0.1 to less than 100 vol. % nitrogen at a temperature in the range of from 250° to 420° C. for 0.5 to 24 hours and to reduce the amount of chloride in the catalyst from 70 to over 90%.

11. The method according to claim 10 wherein the phosphorus/vanadium/oxygen mixed oxide oxidation catalysts comprise a composition of the formula:

$$VP_aZn_bMo_cLi_dO_x$$

wherein a is 0.90 to 1.3, b is 0.001 to 0.15, c is 0.005 to 0.10 and d is 0.001 to 0.15 and x is an determinate number.

* * * * *

UNITED STATES PATENT AND TRADEMARK OFFICE
CERTIFICATE OF CORRECTION

PATENT NO. : 5,446,000
DATED : August 29, 1995
INVENTOR(S) : Arie Bortinger

It is certified that error appears in the above—identified patent and that said Letters Patent is hereby corrected as shown below:

Column 8, line 67 - "FIG. 1." should be -- the FIGURE--

Column 10, claim 6, line 1 - "i" should be --1--

Signed and Sealed this

Ninth Day of January, 1996

Attest:

BRUCE LEHMAN

Attesting Officer    Commissioner of Patents and Trademarks